(12) United States Patent
Ferrer

(10) Patent No.: US 10,874,650 B1
(45) Date of Patent: *Dec. 29, 2020

(54) ANTIVIRAL AND VIRUCIDAL NASAL SPRAY COMPOSITIONS AND RELATED TREATMENT METHODS

(71) Applicant: Ferrer Medical Innovations, LLC, Aventura, FL (US)

(72) Inventor: Gustavo Ferrer, Aventura, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/924,683

(22) Filed: Jul. 9, 2020

Related U.S. Application Data

(60) Provisional application No. 63/015,415, filed on Apr. 24, 2020.

(51) Int. Cl.
| | | |
|---|---|---|
| *A61K 31/4402* | (2006.01) | |
| *A61P 31/14* | (2006.01) | |
| *A61K 9/00* | (2006.01) | |
| *A61K 47/46* | (2006.01) | |
| *A61K 31/56* | (2006.01) | |
| *A61K 47/18* | (2017.01) | |
| *A61K 47/26* | (2006.01) | |

(52) U.S. Cl.
CPC ........ *A61K 31/4402* (2013.01); *A61K 9/0043* (2013.01); *A61K 31/56* (2013.01); *A61K 47/186* (2013.01); *A61K 47/26* (2013.01); *A61K 47/46* (2013.01); *A61P 31/14* (2018.01)

(58) Field of Classification Search
CPC ............ A61K 2300/00; A61K 31/4402; A61K 31/496; A61K 31/7004; A61K 45/00; A61K 45/06; A61K 47/26; A61K 9/0043; A61P 31/16

See application file for complete search history.

(56) References Cited

U.S. PATENT DOCUMENTS

| | | | | |
|---|---|---|---|---|
| 6,054,143 A | * | 4/2000 | Jones ...................... | A61P 31/04 424/434 |
| 2004/0235807 A1 | * | 11/2004 | Weinrich ................ | A61K 31/58 514/171 |
| 2006/0216353 A1 | * | 9/2006 | Liversidge ............. | A61K 9/008 424/489 |
| 2008/0058421 A1 | * | 3/2008 | Lopes .................. | A61K 31/194 514/574 |

* cited by examiner

*Primary Examiner* — Savitha M Rao
(74) *Attorney, Agent, or Firm* — Albert Bordas, P.A.

(57) ABSTRACT

Compositions for treatment or prevention of viral infections, such as influenza A and B, coronaviruses, including but not limited to COVID-19, and rhinoviruses, along with related treatment methods. Certain compositions according to preferred embodiments of the invention may comprise chlorpheniramine, xylitol, and other inactive ingredients, such as aloe vera and/or grapefruit seed extract.

13 Claims, No Drawings

ANTIVIRAL AND VIRUCIDAL NASAL SPRAY COMPOSITIONS AND RELATED TREATMENT METHODS

OTHER RELATED APPLICATIONS

The present application claims priority of pending U.S. Provisional Application No. 63/015,415, filed on Apr. 24, 2020, which is hereby incorporated by reference.

BACKGROUND OF THE INVENTION

1. Field of the Invention

The present invention relates to antiviral and virucidal compositions, and more particularly, to antiviral and virucidal spray compositions for the treatment of viral infection such as colds, influenza A and B, coronaviruses, and rhinoviruses.

2. Description of the Related Art

Chlorpheniramine shows a potent inhibitory activity against divergent influenza A strains and influenza B strain and it protects mice from fatal challenge of avian H7N9 influenza virus. Chlorpheniramine also has been shown to inhibit influenza virus infections by targeting the early stage of virus life cycle, viral entry into the host cells. Chlorpheniramine has also been demonstrated to be superior to Oseltamivir (Tamiflu) in treating Influenza A/B.

Applicant is not aware of any antiviral and virucidal nasal spray composition and related treatment methods having the novel features of the present invention.

SUMMARY OF THE INVENTION

The present invention is referred to compositions that may be used to treat various conditions, particularly conditions caused by viruses, including, for example, colds, influenza A and B, coronaviruses (including but not limited to COVID-19), rhinoviruses, and the like and/or may otherwise provide an antiviral effect, virucidal effect, and/or be preventative of viral disease. Some compositions and treatment methods disclosed herein may also be used to treat allergy symptoms, such as nasal drip, coughing, sneezing, sinusitis, and the like. Some embodiments and implementations may utilize chlorpheniramine individually or in combination with xylitol and/or other excipients. Pharmaceutically-acceptable intranasal carrier such as aqueous saline solution carriers and water. A solution, which contain sodium chloride as the salt. Minor amounts of other ingredients such as pH adjusters (e.g., bicarbonate), emulsifiers or dispersing agents, buffering agents, preservatives, wetting agents and gelling agents may also be present. Most preferably, the nasal composition is isotonic with a pH greater than 6.4. Other pharmaceutically-acceptable nasal excipients that will work as consistency aids are low molecular weight mono- and polyols and are selected from the group consisting of monosaccharides such as glucose (dextrose), fructose (levulose); disaccharides such as sucrose, lactose, maltose, cellobiose and other sugars, ribose, glycerine, sorbitol, xylitol, inositol, propylene glycol, galactose, mannose, xylose, rhamnose, glutaraldehyde, invert sugars, mannitol, polyethylene glycol, glycerol, and mixtures. These compounds provide enhanced physical stability and will reduce or delay the mucociliary clearance patterns of the nasal cycle. These consistency aids are present at a level of from about 0.1% to about 50% by weight of the composition, preferably from about 1% to about 15%, more preferably from about 5% to about 12% by weight. The nasal spray pump Droplet Size Diameter is greater than 5 microns specific for intranasal delivery.

In preferred embodiments and implementations of related methods, the composition may be provided in the form of a nasal spray and/or be delivered into a subject's nasal and/or sinus passages. However, it is anticipated that alternative embodiments and implementations may be made into suspensions, lozenges, tablets, capsules, topical formulations, and/or ingestible products, such as teas or other beverages, for example, or other liquid formulations that may be inserted into nasal passages and/or nasopharyngeal area other than in the form of a spray, such as drops.

In a more particular example of a treatment method according to some implementations, the method may comprise a method for treating a viral infection, such as influenza A and B, coronaviruses, including but not limited to COVID-19, rhinoviruses, and any other viruses obtaining a nasal spray composition comprising chlorpheniramine maleate (referred to herein as chlorpheniramine), in some embodiments and implementations including other ingredients, such as xylitol or another non-hexose sugar alcohol, grapefruit seed extract (GSE), and/or a corticosteroid, such as fluticasone propionate.

In some such embodiments, the composition may comprise chlorpheniramine in a concentration of between about 0.014% and about 10% by mass, in more preferred compositions, between about 0.4% and about 1% by mass, and xylitol in a concentration of between about 5% and about 15% by mass, and GSE in a concentration of between 0.1% to 2%. Other ingredients, such as fluticasone propionate, may be present in a concentration of between about 0.03% and about 1.0% by mass.

The nasal spray composition may then be delivered into the human subject's nasal passages to treat a viral infection and/or prevent a viral infection.

In some implementations, the nasal spray composition may further comprise at least one of benzalkonium chloride and grapefruit seed extract.

In some implementations, the step of delivering the nasal spray composition may comprise delivering 1-2 sprays of the composition in each nostril every six, eight, or twelve hours.

In an example of a composition, such as a nasal spray composition, which may be used for treatment of viral infections, the composition may comprise an antihistamine, such as chlorpheniramine, which may be present in the composition in a concentration of between about 0.1% and about 10%, in more preferred compositions, between about 0.25% and about 4% by mass. The composition may further comprise xylitol or another suitable non-hexose sugar alcohol. The xylitol and/or other sugar alcohol(s) may be present in the composition in a concentration of between about 5% and about 15% by mass. In some embodiments, the xylitol and/or other sugar alcohol(s) may be present in the composition in a concentration of between about 10% and about 15% by mass. The composition may further comprise a corticosteroid, such as fluticasone propionate, which may be present in the composition in a concentration of between about 0.01% and about 3% by mass.

In some embodiments, fluticasone propionate may be present in the composition in a concentration of between about 0.03% and about 1.0% by mass.

In embodiments in which the antihistamine comprises chlorpheniramine, the chlorpheniramine may be present in the composition in a concentration of between about 0.014% and about 10% by mass, in more preferred compositions, between about 0.4 and about 1.0% by mass.

Some embodiments may further comprise aloe Vera, which preferably may be present in the composition in a concentration of between about 0.02% and about 3.0% by mass. In some such embodiments, the aloe Vera may be present in the composition in a concentration of between about 0.05% and about 2.0% by mass.

The features, structures, steps, or characteristics disclosed herein in connection with one embodiment or implementation may be combined in any suitable manner in one or more alternative embodiments or implementations. It should also be understood that any reference to a detail associated with an "embodiment" may be incorporated into and/or used with an "implementation," and vice versa.

The present invention is an antiviral and virucidal nasal spray composition comprising chlorpheniramine maleate in a concentration between about 0.01% and about 10% by mass; and a sugar alcohol selected from the group consisting of xylitol, xylose, erythritol, ribose, and arabinose and others. The sugar alcohol is in a concentration between about 5% and about 15% by mass.

In a preferred embodiment, the sugar alcohol is xylitol in a concentration between about 10% to about 15% by mass, and the chlorpheniramine maleate is in a concentration between about 0.25% to about 4% by mass.

The antiviral and virucidal nasal spray composition further comprises a corticosteroid selected from the group consisting of mometasone, fluticasone propionate, fluticasone furoate, triamcinolone acetonide, and/or budesonide glucocorticoid in a concentration between about 0.01 and about 3% by mass. In a preferred embodiment, the corticosteroid is fluticasone propionate in a concentration between about 0.03% and about 1.0% by mass.

The antiviral and virucidal nasal spray compositions further comprises of the benzalkonium chloride and grapefruit seed extract in a concentration between about 0.05% and about 0.2% by mass, and between about 0.01 and about 3% by mass respectively.

The antiviral and virucidal nasal spray composition is used in the treatment of viral infections selected from the group consisting of colds, influenza A and B, coronaviruses, and rhinoviruses. In a preferred embodiment, the antiviral and virucidal nasal spray compositions are used in the treatment of coronavirus.

A method of treating viral infections in a subject in need of such treatment, the method comprising administering to the subject a nasal spray composition by delivering into nasal passages. The nasal spray composition comprising chlorpheniramine maleate in a concentration between 0.01% and 10% by mass, xylitol in a concentration between 5% to 15% and GSE in a concentration between 0.01% and 3%.

In a preferred embodiment, the chlorpheniramine maleate in a concentration between 0.15% and 4% by mass, and in a more preferred embodiment the chlorpheniramine maleate is in a concentration between about 0.4% and about 1% by mass.

The nasal spray composition further comprises fluticasone propionate in a concentration between about 0.03% and about 1.0% by mass. The nasal spray composition further comprises at least one of the benzalkonium chloride in a concentration between about 0.05% and about 0.2% by mass, or grapefruit seed extract in a concentration of between about 0.01% and about 3% by mass.

The nasal spray composition is administering by delivering 1-2 sprays of the composition in each nostril every four, six, eight, or twelve hours.

The viral infection is selected from the group consisting of colds, influenza A and B, coronaviruses (including COVID-19), rhinoviruses and other respiratory viruses. In a preferred embodiment, the viral infection is coronavirus.

A method of treating coronaviruses in a subject in need of such treatment, the method comprising administering to the subject a nasal spray composition by delivering into nasal passages. The nasal spray composition comprising chlorpheniramine maleate in a concentration between about 0.4% and about 1% by mass, xylitol in a concentration between about 10% and about 15% by mass and grapefruit seed extract in a concentration of between about 0.01% and about 3% by mass The nasal spray composition further comprises at least one of the following components fluticasone propionate in a concentration between about 0.03% and about 1.0% by mass; benzalkonium chloride in a concentration between about 0.05% and about 0.2% by mass, and grapefruit seed extract in a concentration between about 0.01 and about 3% by mass.

The nasal spray composition may further comprises Oat Beta Glucan between 0.10 and 30%; Tea Tree Oil between 0.02 and 10%; *Eucalyptus* Oil between 0.02 and 10%; Oregano Oil between 0.01 and 10%; Parsley Oil between 0.01 and 10%; and Pau D'Arco between 0.01 and 10%.

It is therefore one of the main objects of the present invention to provide antiviral and virucidal nasal spray compositions and related treatment methods.

It is another object of this invention to provide antiviral and virucidal nasal spray compositions and related treatment methods, which comprise chlorpheniramine maleate.

It is another object of this invention to provide antiviral and virucidal nasal spray compositions and related treatment methods, which is effective against COVID-19.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

The present invention is referred to antiviral and virucidal nasal spray compositions and related treatment methods. Disclosed herein are various compositions that may be provided in nasal sprays and/or otherwise delivered into a subject's nasal and/or sinus passages. Preferred embodiments of such compositions, and preferred implementations of related methods, may be used to treat and/or prevent various conditions caused by viruses, including colds, influenza, coronaviruses, rhinoviruses, or other viral infections. Some embodiments may also allow for restoring and/or improving the natural flora of the nasal cavity to provide more long-lasting health improvements. However, it is anticipated that alternative embodiments and implementations may be made into suspensions, lozenges, tablets, capsules, topical formulations, and/or ingestible products, such as teas or other beverages, for example.

As demonstrated by the working example below (Example 1), the present inventor has demonstrated that in vitro chlorpheniramine with xylitol is highly effective against COVID-19. The composition tested eliminated more than 80% of the viral load in a virucidal assay that tested COVID-19 from the United States and Wuhan China.

In addition, to treating or prevent viral infections, the preferred compositions and treatment methods disclosed herein may combine the most desirable agents and concentrations into a single composition, preferably in the form of a nasal spray, and may include other ingredients for decreasing various side effects, such as xylitol or another non-hexose sugar alcohol, which may provide a number of benefits, such as inhibiting bacterial growth, fungal growth, decreasing undue nasal drying, enhancing anti-inflammatory benefits, enhancing anti-viral effects, and/or decreasing the unwanted aftertaste of the product.

In most preferred compositions and related treatment methods, an antihistamine is provided, such as, in preferred embodiments, chlorpheniramine. The chlorpheniramine may be present in the formulation in a concentration between about 0.01 and about 10% by mass, more preferably, between about 0.25 and about 4% by mass. In more preferred embodiments, the chlorpheniramine may be present in the formulation in a concentration between about 2% and about 3% by mass.

In some compositions and related treatment methods, one or more corticosteroids or other intranasal steroids are included in the formulation. For example, in preferred embodiments, mometasone, fluticasone propionate, fluticasone furoate, triamcinolone acetonide, and/or budesonide glucocorticoid may be included. The corticosteroid may be present in the formulation in a concentration between about 0.01 and about 3% by mass, and may comprise, for example, fluticasone propionate. In some such formulations, the fluticasone propionate may be present in a concentration of between about 0.03% and about 1% by mass. In more preferred formulations, the fluticasone propionate may be present in a concentration of about 0.05% by mass.

In most preferred compositions, xylitol or, alternatively, another non-hexose sugar alcohol, such as xylose, erythritol, ribose, and/or arabinose, may be included in the formulation. Including xylitol or another such ingredient may provide a number of benefits and may provide a synergistic effect with the other ingredients of the formulation in treating and/or preventing viral infections and may provide other improvements to the formulation. Xylitol in particular has been shown to be remarkably effective in eradicating microbes, such as bacteria and viruses, and in moisturizing nasal passages, sinuses, and the like. Without being limited by theory, this is thought to occur because xylitol can create a hyper-osmotic solution that pulls moisture towards it from surrounding tissues without generated mucous. Thus, the combination of xylitol, or other similar compositions disclosed herein, may result in a decrease in mucous production, potentially along with accompanying anti-bacterial, anti-viral and other health benefits associated with xylitol and/or other similar agents.

Xylitol may also enhance the taste and/or reduce the negative smell/aftertaste issues commonly associated with prior art formulations. Moreover, by providing a sweetener that does not include sugar and serves as an active agent in the formulation, several benefits may be derived. For example, although xylitol acts as a sweetener, unlike typical sweeteners, xylitol enhances the ability of other agents to treat bacterial infections by actively starving the microorganisms causing the symptoms, rather than one that counteracts the active ingredients in a nasal spray or other treatment composition by feeding the microorganisms, or one that only passively starves the microorganisms by providing a sweetener that is not consumed by the more common oral and pharyngeal pathogens. Thus, compositions including xylitol may result in improved ability to treat various symptoms that may be caused by microorganisms (along with other not caused by microorganisms) and, more importantly, to fight the bacterial, viral, and/or other microorganisms behind these symptoms.

Preferably, xylitol or, alternatively one of the other preferably non-hexose sugar alcohols disclosed herein (erythritol, for example), is present in a concentration of between about 5 and about 15% by mass. In more preferred formulations, xylitol may be present in a concentration of between about 10 and about 15% by mass. Although xylitol has been used as a sweetener in a variety of products, it should be noted that it is considered an active ingredient in the preferred formulations of the invention disclosed herein due to its moisturizing, antiviral, and/or antibacterial properties.

More preferred formulations for use in connection with preferred treatment methods may include various other ingredients, such as aloe Vera. Including aloe Vera, preferably along with xylitol, may enhance the synergistic effects referenced elsewhere herein. More particularly, aloe Vera may provide a soothing, moisturizing, and/or cooling effect that may increase user compliance and/or may heal irritated tissue, such as nasal and/or sinus passages in preferred embodiments, which may be caused by, for example, repeated nose wiping, sneezing, nose blowing, and the like. In preferred formulations, aloe Vera is present in a concentration of between about 0.05 and about 3.0% by mass.

Some formulations may include other ingredients, such as grapefruit see extract, benzalkonium chloride, and/or glycerine, preferably along with purified water. Thus, in some such embodiments, grapefruit seed extract may be included in the formulation in an amount between about 0.01 and about 3% by mass. Glycerine, if included, preferably ranges between about 0.05 and about 3% by mass. In embodiments comprising benzalkonium chloride, which may be a suitable substitute for grapefruit seed extract, may be present in a concentration of between about 0.05 and about 0.2% by mass. The remainder of the formulation may comprise (preferably purified) water. In some formulations, purified water may be present in a range from about 80 to about 98% by mass. In some such formulations, the purified water may be present in a range from about 80 to about 90% by mass. In a more preferred formulation, water may be present in a concentration of about 87.5%.

Additional more specific and, generally speaking, more preferred, embodiments of the invention are disclosed below. Although these formulations have very specific ingredients and concentrations, it should be understood that the concentrations of the ingredients in these formulations may vary by around 5% from the concentrations provided herein.

Example 1

In a first working example of a study testing the efficacy of certain formulations disclosed herein, a nasal spray composition was obtained comprising chlorpheniramine maleate at 3.6 mg/mL or 0.4% concentration. The composition further comprised xylitol at a concentration of about 11% by mass, glycerin, GSE of 0.2%, sodium bicarbonate, and purified water.

A viral stock of SARS-CoV-2, USA-WA1/2020 strain, was prepared before testing through growth in Vero 76 cells. The culture medium for the prepared stock (test medium) was MEM with 2% fetal bovine serum and 50 μg/mL gentamicin.

The composition was mixed directly with virus solution at a proportion of about 90% compound preparation and 10% virus solution. A single concentration was tested in triplicate. Test medium without virus was added to one tube of the prepared composition to serve as a toxicity control. Ethanol (70%) was tested in parallel as a positive control, and water only was tested as a virus control. The solution and virus were incubated at room temperature (22±2° C.) for 25 minutes. The solution was then neutralized through 1/10 dilution in a test medium.

Surviving virus from each sample was then quantified with standard end-point dilution assays. More particularly, samples were serially diluted 1/10 in the test medium. Then, 100 μL of each dilution was plated into quadruplicate wells of 96-well plates containing 80-90% confluent Vero 76 cells. The plates were then incubated at 37±2° C. under 5% CO2 for six days. Each well was then scored for the presence or absence of virus. The end-point titer (CCID50) values were calculated with the Reed-Muench (1948) equation, with which those of ordinary skill in the art are familiar. A statistical analysis was then performed. In particular, three independent replicates of each sample were tested, and the average and standard deviation were calculated. Results were compared with untreated controls by one-way ANOVA with Dunnett's multiple comparison test in GraphPad Prism (version 8) software.

Virus controls were tested in water, and the reduction of virus in the test wells compared with the virus control wells was calculated as the log reduction value (LRV). Toxicity controls were tested with medium not containing virus to determine whether the samples were toxic to cells. Neutralization controls were tested to ensure that viral inactivation did not continue after the specified contact time and that any residual sample in the titer assay plates did not inhibit growth and detection of surviving virus.

This procedure was performed by adding toxicity samples to titer test plates and then spiking each well with a small amount of virus that would produce an observable cytopathogenic effect during the incubation period.

Table A, which is reproduced below, illustrates the virucidal efficacy of the nasal spray composition used in the study of Example 1 against SARS-CoV-2 after a 25-minute incubation with virus at 22±2° C. This table shows the viral titer and LRV values for SARS-CoV-2 after incubation with a single concentration of the nasal composition used in the study.

TABLE A

|  | Concentration | Incubation | Virus Titer | Log Reduction Value |
|---|---|---|---|---|
| Nasal Spray | 90% | 25 minutes | 1.7 ± 0.0 | 2.5*** |
| Ethanol | 67.5% | 25 minutes | 1.0 ± 0.6 | 3.2*** |
| Virus Control | N/A | 25 minutes | 4.2 ± 0.4 | N/A |

The Virus Titer in Table A was taken using Log10 CCID50/mL which is defined as 50% cell culture infectious dose per mL of the virus per 0.1 mL and is the average of three replicates ± standard deviation. Similarly, the Log Reduction Value in Table A is the reduction of virus compared with that of the virus control
***P < 0.001 by one-way ANOVA and Dunnett's post-test, compared with untreated virus control (water). For wells with undetectable virus a value equal to the lower limit of detection was assigned for statistical analyses.

The results of the study of Example 1 demonstrate that toxicity was observed in the top dilution (1/10). Virus was observed below that dilution and therefore did not affect calculations of viral titer or LRV. After a 25-minute contact time, the nasal spray reduced the levels of virus from 4.2 to 1.7 log 10 CCID50 per 0.1 mL, a statistically significant reduction of 2.5 log 10 CCID50. Neutralization controls demonstrated that the residual sample did not inhibit viral growth and detection in the endpoint titer assays. Virus controls and positive controls performed as expected in the study.

This working example demonstrates the strong virucidal effect against SARS-CoV-2 of a nasal spray containing chlorpheniramine. The present inventor believes that combining the tested solution with chloroquine and/or hydroxychloroquine may further enhance efficacy.

Example 2

In another more particular example of a composition, preferably in the form of a nasal spray or nebulized, and/or related treatment method for treating or preventing viral infections, the composition may comprise the following ingredients in at least approximately the concentrations (by mass) presented in the chart below. However, as mentioned above, these concentrations may vary by 5% in certain alternative embodiments and related methods. Similarly, one or more of these ingredients may be omitted and/or replaced with an alternative substantially similar ingredient available to those of ordinary skill in the art in still other embodiments and related methods.

| Oat Beta Glucan | 0.10 to 30% |
|---|---|
| Tea Tree Oil | 0.02 to 10% |
| Eucalyptus Oil | 0.02 to 10% |
| Oregano Oil | 0.01 to 10% |
| Parsley Oil | 0.01 to 10% |
| Pau D'Arco | 0.01 to 10% |

Example 3

In another more particular example of a composition, preferably in the form of a nasal spray, and/or related treatment method for treating or preventing viral infections, the composition may comprise the following ingredients in at least approximately the concentrations (by mass) presented in the chart below. However, as mentioned above, these concentrations may vary by 5% in certain alternative embodiments and related methods. Similarly, one or more of these ingredients may be omitted and/or replaced with an alternative substantially similar ingredient in still other embodiments and related methods.

| Chlorpheniramine | 0.4% |
|---|---|
| Mometasone | 0.05% |
| Xylitol | 11% |
| Grapefruit Seed Extract | 0.2% |
| Glycerine | 1% |
| Purified Water | 87.5% |

Because this is a more potent formulation than that of Example 2, in certain implementations of treatment methods involving this composition, the composition may be delivered into a subject's nasal cavity every four to six hours, preferably in the form of 1-2 sprays in each nostril. The present inventor has found that doing so is highly effective in drying the nasal mucosa, reducing inflammation, and/or restoring the natural, nasal flora. It can therefore also be used to treat, for example, acute or chronic sinusitis and related conditions, including nasal drip, cough, and nasal dryness.

Example 4

In another more particular example of a composition, preferably in the form of a nasal spray, and/or related treatment method for treating or preventing viral infections, the composition may comprise the following ingredients in at least approximately the concentrations (by mass) presented in the chart below. However, as mentioned above, these concentrations may vary by 5% in certain alternative embodiments and related methods. Similarly, one or more of these ingredients may be omitted and/or replaced with an alternative substantially similar ingredient in still other embodiments and related methods.

| | |
|---|---|
| Chlorpheniramine | 0.014 to 10% (more preferably 0.4 to 1.0%) |
| Xylitol | 10 to 15% |
| Benzalkonium Chloride | 0.02 to 0.05 |
| Glycerine | 1 to 2% |
| Purified Water | 80 to 90% |
| Grapefruit Seed Extract | 0.01 to 3% |

Because this is a more potent formulation than that of Example 2, in certain implementations of treatment methods involving this composition, the composition may be delivered into a subject's nasal cavity every four to six hours, preferably in the form of 1-2 sprays in each nostril. The present inventor has found that doing so is highly effective in drying the nasal mucosa, reducing inflammation, and/or restoring the natural, nasal flora. It can therefore also be used to treat, for example, acute or chronic sinusitis and related conditions, including nasal drip, cough, and nasal dryness.

Example 5

In yet another even more particular example of a composition, preferably in the form of a nasal spray, and/or related treatment method for treating or preventing viral infections the composition may comprise the following ingredients in at least approximately the concentrations (by mass) presented in the chart below.

| | |
|---|---|
| Chlorpheniramine | 0.014% to 10% (in more particular compositions, 0.4%) |
| Fluticasone propionate | 0.03 to 1% |
| Xylitol | 10 to 15% |
| Grapefruit Seed Extract (GSE) | 0.01 to 3% |
| Benzalkonium chloride | 0.02 to 0.05% |
| Glycerine | 1 to 2% |
| Purified Water | 80 to 90% |

Example 6

In another example of a composition according to other embodiments, preferably in the form of a nasal spray, and/or related treatment method for treating or preventing viral infections, the composition may comprise the following ingredients in at least approximately the concentrations (by mass) presented in the chart below.

| | |
|---|---|
| Chlorpheniramine | 0.014 to 10.0% |
| Fluticasone propionate | 0.03 to 1% |
| Grapefruit Seed Extract (GSE) | 0.01 to 3% |
| Benzalkonium chloride | 0.02 to 0.05% |
| Glycerine | 1 to 2% |
| Purified Water | 80 to 90% |

Example 7

In still another example of a composition according to other embodiments, preferably in the form of a nasal spray, and/or related treatment method for treating or preventing viral infections, the composition may comprise the following ingredients in at least approximately the concentrations (by mass) presented in the chart below.

| | |
|---|---|
| Chlorpheniramine | 0.014 to 10.0% |
| Grapefruit Seed Extract (GSE) | 0.01 to 3% |
| Benzalkonium chloride | 0.02 to 0.05% |
| Glycerine | 1 to 2% |
| Purified Water | 80 to 90% |

Example 8

In yet still another example of a composition according to other embodiments, preferably in the form of a nasal spray, and/or related treatment method for treating or preventing viral infections, the composition may comprise the following ingredients in at least approximately the concentrations (by mass) presented in the chart below.

| INGREDIENT | PERCENTAGE BY WEIGHT |
|---|---|
| Chlorpheniramine | 0.014 to 10.0% |
| Grapefruit Seed Extract (GSE) | 0.01 to 3% |
| Benzalkonium chloride | 0.02 to 0.05% |
| Glycerine | 1 to 2% |
| Sodium Bicarbonate | 0.10 to 30% |
| Oat Beta Glucan | 0.10 to 30% |
| Tea Tree Oil | 0.02 to 10% |
| Eucalyptus Oil | 0.02 to 10% |
| Oregano Oil | 0.01 to 10% |
| Parsley Oil | 0.01 to 10% |
| Pau D'Arco | 0.01 to 10% |

It will be understood by those having skill in the art that changes may be made to the details of the above-described embodiments without departing from the underlying principles presented herein. For example, the compositions disclosed herein may be administered via liquid drops from a dropper, topically (in some cases using a cotton swab or the like), orally, via a mister or atomizer, nebulization, and/or via any other suitable manner of administration. In addition, alternative compositions and treatment methods are contemplated in which the preferred nasal sprays may be replaced with suspensions, lozenges, tablets, capsules, topical formulations, and/or ingestible products, such as teas or other beverages, for example. In addition, any suitable combination of various embodiments, or the features thereof, is contemplated.

Any methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element.

The virucidal effect of the composition was proven to be effective in a study performed at Utah State University. The study is incorporated herein by reference.

REFERENCES

G. Ferrer, J. Westover, "In Vitro Virucidal Effect of Intranasally Delivered Chlorpheniramine Maleate Compound Against Severe Acute Respiratory Syndrome Coronavirus 2 (SARS-CoV-2)", Utah State University, Institute for Antiviral Research and Ferrer Medical Innovations Nova Southeastern University, May 2020.

What is claimed is:

1. An antiviral and virucidal nasal spray composition comprising:
   A) chlorpheniramine maleate in a concentration between about 0.01% and about 10% by mass;
   B) xylitol in a concentration between about 10% to about 15% by mass; and
   C) grapefruit seed extract in a concentration between about 0.01 and about 3% by mass.

2. The antiviral and virucidal nasal spray composition set forth in claim 1, further characterized in that said chlorpheniramine maleate is in a concentration between about 0.25% to about 4% by mass.

3. The antiviral and virucidal nasal spray composition set forth in claim 1, further characterized in that further comprises a corticosteroid selected from the group consisting of mometasone, fluticasone propionate, fluticasone furoate, triamcinolone acetonide, and/or budesonide glucocorticoid, in a concentration between about 0.01 and about 3% by mass.

4. The antiviral and virucidal nasal spray composition set forth in claim 3, further characterized in that said corticosteroid is fluticasone propionate in a concentration between about 0.03% and about 1.0% by mass.

5. The antiviral and virucidal nasal spray composition set forth in claim 1 used in the treatment of viral infections selected from the group consisting of colds, influenza A and B, coronaviruses specially COVID-19, and rhinoviruses.

6. A method of treating viral infections in a subject in need of such treatment, the method comprising administering to said subject a nasal spray composition by delivering into nasal passages, said nasal spray composition comprising:
   A) chlorpheniramine maleate in a concentration between 0.01% and 10% by mass;
   B) xylitol in a concentration between 10% to 15% by mass; and
   C) grapefruit seed extract in a concentration between about 0.01% and about 3% by mass.

7. The method set forth in claim 6, further characterized in that said chlorpheniramine maleate is in a concentration between 0.25% and 4% by mass.

8. The method set forth in claim 6, further characterized in that said chlorpheniramine maleate is in a concentration between about 0.4% and about 1% by mass.

9. The method set forth in claim 6, further characterized in that said nasal spray composition further comprises fluticasone propionate in a concentration between about 0.03% and about 1.0% by mass.

10. The method set forth in claim 6, further characterized in that said nasal spray composition is administering by delivering 1-2 sprays of the composition in each nostril every six, eight, or twelve hours.

11. The method set forth in claim 6, further characterized in that said viral infection is selected from the group consisting of colds, influenza A and B, coronaviruses, and rhinoviruses.

12. The method set forth in claim 6, further characterized in that said viral infection is coronavirus.

13. A method of treating coronaviruses in a subject in need of such treatment, the method comprising administering to said subject a nasal spray composition by delivering into nasal passages, said nasal spray composition comprising:
   A) chlorpheniramine maleate in a concentration between about 0.4% and about 1% by mass;
   C) fluticasone propionate in a concentration of between about 0.03% and about 1.0% by mass; and
   E) grapefruit seed extract in a concentration between about 0.01 and about 3% by mass.

* * * * *